United States Patent
Sadakane et al.

(10) Patent No.: US 9,456,964 B2
(45) Date of Patent: *Oct. 4, 2016

(54) ION SUSTAINED-RELEASE DENTAL RESIN TEMPORARY SEALING MATERIAL COMPOSITION

(71) Applicant: SHOFU INC., Kyoto (JP)

(72) Inventors: Yuji Sadakane, Kyoto (JP); Katsura Ishikawa, Kyoto (JP); Toshiyuki Nakatsuka, Kyoto (JP)

(73) Assignee: SHOFU INC., Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/593,241

(22) Filed: Jan. 9, 2015

(65) Prior Publication Data

US 2015/0342840 A1 Dec. 3, 2015

(30) Foreign Application Priority Data

May 30, 2014 (JP) ................. 2014-113577

(51) Int. Cl.
*A61K 6/083* (2006.01)
*A61K 6/00* (2006.01)

(52) U.S. Cl.
CPC ........... *A61K 6/0835* (2013.01); *A61K 6/0091* (2013.01)

(58) Field of Classification Search
CPC ............................ A61K 6/0276; A61K 6/083
USPC ............................................ 523/118; 106/35
See application file for complete search history.

(56) References Cited

U.S. PATENT DOCUMENTS

| 5,147,202 A | 9/1992 | Masuhara et al. |
| 5,883,153 A * | 3/1999 | Roberts ................ A61K 6/0017 501/151 |
| 6,583,197 B1 | 6/2003 | Wada et al. |
| 2003/0050359 A1 | 3/2003 | Kimura et al. |
| 2009/0068123 A1 | 3/2009 | Takei et al. |
| 2011/0070563 A1* | 3/2011 | Ori ...................... A61K 6/0038 433/224 |

FOREIGN PATENT DOCUMENTS

| JP | 2002-114620 A | 4/2002 |
| JP | 3418056 B2 | 6/2003 |
| JP | 2010-215538 A | 9/2010 |

OTHER PUBLICATIONS

Oct. 6, 2015 Extended European Search Report issued on European Patent Application No. 15150487.5.
Oct. 12, 2015 Extended European Search Report issued in European Patent Application No. 15150317.4.

* cited by examiner

*Primary Examiner* — Tae H Yoon
(74) *Attorney, Agent, or Firm* — Wenderoth, Lind & Ponack, L.L.P.

(57) ABSTRACT

A dental resin temporary sealing material composition that is excellent in adhesion to the tooth substance and removability of the hardened material and has a preventive function of releasing various ions including a fluoride ion is provided. The adhesion to cavity walls can be improved and, since there is little dimensional change during hardening, excellent sealability in a cavity can be attained.

4 Claims, No Drawings

ION SUSTAINED-RELEASE DENTAL RESIN TEMPORARY SEALING MATERIAL COMPOSITION

TECHNICAL FIELD

The present invention relates to a dental resin temporary sealing material composition. The present invention particularly relates to a dental resin temporary sealing material composition that is excellent in adhesion to the tooth substance and removability of the hardened material and has a preventive function of releasing various ions including a fluoride ion.

BACKGROUND ART

A dental resin temporary sealing material is a provisional filling material used to, after removing caries that have occurred in a tooth and forming a cavity, temporarily seal the cavity in dental treatment. Conventional dental resin temporary sealing materials are mainly classified into two types, i.e. photopolymerization type and chemical polymerization type. In current clinical practice, a dentist selects one of the types and uses the selected type depending on the case, the site, the application period, etc. The chemical polymerization type is widely used in terms of cost and ease of filling operation and removal operation. Chemical polymerization type resin temporary sealing materials are, however, defective in sealability. Cases where the tooth substance is decalcified by plaque invasion from the marginal region have been confirmed in actual clinical practice, generating concerns about the occurrence of post-operative pain or secondary caries after prosthesis attachment.

Patent Document 1 discloses a resin temporary sealing material that contains rosin or sandarac to improve the adhesion to cavity walls and exhibit excellent sealability. Merely containing rosin or sandarac in the resin temporary sealing material, however, causes a decrease in material property and tends to induce deformation of the hardened material due to mastication, though the adhesion to cavity walls is improved. As a result, a gap occurs in the marginal region, creating a situation where plaque invades and decalcifies the tooth substance easily.

Patent Document 2 discloses a photopolymerization type resin temporary sealing material that contains a rosin cyclic terpene acid to improve the removability. However, the hardened material of a photopolymerization type resin temporary sealing material becomes too hard and is difficult to be removed using an instrument. Besides, there is a risk that the cavity wall tooth substance around the hardened material is destroyed during removal.

PRIOR ART DOCUMENT

Patent Document

1: Japanese Patent No. 3418056
2: Japanese Unexamined Patent Application Publication No. 2010-215538

SUMMARY OF INVENTION

Technical Problem

There is a need for a resin temporary sealing material that has both excellent sealability of enabling temporary sealing for a predetermined period in a cavity while adhering to cavity walls and excellent removability of enabling easy removal of the temporary sealing material upon removal, and can suppress decalcification of the tooth substance in the cavity by releasing various ions including a fluoride ion.

Solution to Problem

The present invention is a dental resin temporary sealing material composition that is polymerizable, the dental resin temporary sealing material composition including: (a) 44% to 64% by weight a noncrosslinked (meth)acrylate polymer; (b) 3% to 21% by weight a filling material; (c) 4% to 16% by weight a monofunctional (meth)acrylate polymerizable monomer; (d) 4% to 13% by weight a hydrophilic polymerizable monomer; (e) 0.1% to 5% by weight a polymerization initiator; and (f) 5% to 25% by weight a plasticizer, wherein the noncrosslinked (meth)acrylate polymer (a) is particulate, and has a 50% average particle diameter in a range of 5 μm to 150 μm, and a weight-average molecular weight in a range of 50000 to 1500000, and the hydrophilic polymerizable monomer (d) has solubility of 5% by weight or more, in water at 23° C.

Moreover, a part or whole of the filling material (b) included in the dental resin temporary sealing material composition is ion sustained-release glass.

Preferably, the ion sustained-release glass sustained-releases a fluoride ion, and further sustained-releases at least one type of ion from among bivalent to tetravalent ions.

Preferably, the ion sustained-release glass sustained-releases a fluoride ion, and further sustained-releases at least one type from among a strontium ion, an aluminum ion, and a borate ion.

Advantageous Effect of Invention

The dental resin temporary sealing material composition according to the present invention includes the filling material, the hydrophilic polymerizable monomer, and the plasticizer. Hence, the adhesion to cavity walls can be improved and, since there is little dimensional change during hardening, excellent sealability in a cavity can be attained. In addition, the dental resin temporary sealing material composition has proper flexibility and hardness, and so the material deformation can be minimized even under harsh conditions in the mouth. The dental resin temporary sealing material composition thus has excellent retentivity in the cavity, and excellent removability of enabling easy removal of the hardened material. Since the hardened material is flexible, the biting pressure during mastication involving contact with the antagonist can be alleviated to reduce stimulation. Furthermore, in the case where the dental resin temporary sealing material composition contains the ion sustained-release glass, the dental resin temporary sealing material composition has a preventive function such as suppressing decalcification of the tooth substance by releasing various ions including a fluoride ion toward the tooth substance of the cavity walls.

DESCRIPTION OF EMBODIMENTS

The noncrosslinked (meth)acrylate polymer (a) swells by the monofunctional (meth)acrylate polymerizable monomer (swelling is a phenomenon in that a substance absorbs a solvent and expands. In the dental field, swelling means a sand-like, rice cake-like, or rubber-like thickening behavior as a result of absorption of a monofunctional (meth)acrylate polymerizable monomer into a powder material mainly composed of a (meth)acrylate polymer). As the noncrosslinked (meth)acrylate polymer, a polymer formed by homopolymerization of a (meth)acrylate polymerizable monomer, a polymer formed by copolymerization of a plurality of (meth)acrylate polymerizable monomers, a polymer formed by copolymerization with another polymerizable monomer, or the like can be used without any limitation.

Preferable specific examples of the noncrosslinked (meth)acrylate polymer include: homopolymers such as polymethyl (meth)acrylate, polyethyl (meth)acrylate, polypropyl (meth)acrylate, polyisopropyl (meth)acrylate, polyisobutyl (meth)acrylate, and polybutyl (meth)acrylate; and copolymers that each combine two or more types from among methyl (meth)acrylate, ethyl (meth)acrylate, propyl (meth)acrylate, isopropyl (meth)acrylate, isobutyl (meth)acrylate, butyl (meth)acrylate, and the like. These noncrosslinked (meth)acrylate polymers may be used singly or in combination.

Of these noncrosslinked (meth)acrylate polymers, polymethyl methacrylate, polyethyl methacrylate, or a copolymer of methyl methacrylate and ethyl methacrylate is preferably used.

The polymerization method for such a noncrosslinked (meth)acrylate polymer is not limited. Any polymerization method such as emulsion polymerization, suspension polymerization, or the like is applicable. The shape of the noncrosslinked (meth)acrylate polymer is particulate. Preferable shapes include spherical, crushed, and hollow, without limitation. A particularly preferable shape is spherical. The average particle diameter (50%) of the noncrosslinked (meth)acrylate polymer is not limited so long as it is in the range of 5 μm to 150 μm. A preferable range is 10 μm to 150 μm, and a more preferable range is 20 μm to 140 μm. The weight-average molecular weight of the noncrosslinked (meth)acrylate polymer is not limited so long as it is in the range of 50000 to 1500000. A preferable range is 100000 to 1400000, and a more preferable range is 200000 to 1300000.

The content of the noncrosslinked (meth)acrylate polymer is not limited so long as it is in the range of 44% to 64% by weight. A preferable range is 49% to 64% by weight.

In the case where the content of the noncrosslinked (meth)acrylate polymer is less than 44% by weight, for example, the following problem arises: the monofunctional (meth)acrylate polymerizable monomer or the hydrophilic (meth)acrylate polymerizable monomer is excessive and penetration and swelling are not uniform, which decreases the flexibility of the hardened material and causes the hardened material to become too hard for removal. In the case where the content of the noncrosslinked (meth)acrylate polymer exceeds 64% by weight, for example, the following problem arises: the noncrosslinked (meth)acrylate polymer is excessive and hardening is not uniform, and so the hardened material cannot be removed at once during removal.

The filling material (b) is not particularly limited, and may be any of an organic component, an inorganic component, and their mixture or compound so long as it does not swell by the monofunctional (meth)acrylate polymerizable monomer. Swelling is a phenomenon in that a substance absorbs a solvent and expands. In the dental field, swelling means a sand-like, rice cake-like, or rubber-like thickening behavior as a result of absorption of a monofunctional (meth)acrylate polymerizable monomer into a powder material mainly composed of a (meth)acrylate polymer.

Specific examples of the filling material include: metal hydroxides such as aluminum hydroxide, calcium hydroxide, and magnesium hydroxide; carbonates such as calcium carbonate and strontium carbonate; metal oxides such as aluminum oxide; metal fluorides such as barium fluoride, calcium fluoride, and strontium fluoride; inorganic filling materials such as talc, kaolin, clay, mica, hydroxyapatite, silica, quartz, and various glass (glass such as fluoroaluminosilicate, borosilicate, aluminoborate, and fluoroaluminoborosilicate including fluorine and/or a heavy metal such as sodium, strontium, barium, or lanthanum); elastomers such as polyvinyl acetate, polyvinyl alcohol, and styrene-butadiene rubber; organic filling materials such as a crosslinked (meth)acrylate polymer formed by copolymerizing a monofunctional (meth)acrylate polymerizable monomer and a polymerizable monomer having two or more functional groups; and organic-inorganic composite filling materials such as a filling material obtained by polymerized-coating the surface of an inorganic filling material with a polymerizable monomer, a filling material obtained by mixing and polymerizing an inorganic filling material and a polymerizable monomer and grinding the result into an appropriate particle diameter, and a filling material obtained by dispersing a filling material in a polymerizable monomer beforehand and subjecting it to emulsion polymerization or suspension polymerization, though the filling material is not limited to such. The particle diameter (50%) of the filling material used in the present invention is not particularly limited so long as it is in the range of 0.01 μm to 100 μm. A preferable range is 0.01 μm to 50 μm, and a more preferable range is 0.1 μm to 5 μm. The shape of the filling material is not limited, and may be any shape such as spherical, platy, crushed, and scaly. A preferable shape is spherical or crushed.

In a preferable embodiment, ion sustained-release glass is included as part or whole of the filling material (b), and ions resulting from the glass composition are continuously sustained-released from the glass.

The ion sustained-release glass used in the present invention is not limited so long as it is a glass including at least one type of glass skeleton forming element for forming a glass skeleton and at least one type of glass modifying element for modifying the glass skeleton. In the present invention, an element that can be either a glass skeleton forming element or a glass modifying element depending on the glass composition, namely, a glass amphoteric element, is included in the category of glass skeleton forming elements. Specific examples of the glass skeleton forming element included in the ion sustained-release glass include silica, aluminum, boron, and phosphorus, which may be used singly or in combination. Specific examples of the glass modifying element include: halogen elements such as fluorine, bromine, and iodine; alkali metal elements such as sodium and lithium; and alkaline earth metal elements such as calcium and strontium, which may be used singly or in combination. It is preferable to include silica, aluminum, or boron as the glass skeleton forming element, and fluorine, sodium, or strontium as the glass modifying element. Specific examples are silica glass, fluoroaluminosilicate glass, fluoroborosilicate glass, fluoroaluminoborosilicate glass, and the like including strontium or sodium. Fluoroaluminoborosilicate glass including strontium and sodium is particularly preferable in terms of sustained-releasing the fluoride ion, the strontium ion, the aluminum ion, and the borate ion, and its glass composition range is as follows: $SiO_2$ 15% to 35% by mass, $Al_2O_3$ 15% to 30% by mass, $B_2O_3$ 5% to 20% by mass, SrO 20% to 45% by mass, F 5% to 15% by mass, $Na_2O$ 0% to 10% by mass. This glass composition can be checked by instrumental analysis such as elemental analysis, Raman spectrum analysis, or fluorescence X-ray analysis, where it is only necessary that the actual measurement by any of the analysis methods meets the composition ranges.

The method of manufacturing the glass is not particularly limited, and manufacturing methods such as a melting method and a sol-gel method are applicable. Of these, the melting method using a melting furnace is preferable for ease of glass composition design including raw material selection.

The ion sustained-release glass used in the present invention has an amorphous structure, but may partially include a crystalline structure or be a mixture of glass having an amorphous structure and glass having a crystalline structure. Whether or not the glass structure is amorphous can be determined using an analyzer such as an X-ray diffraction analyzer or a transmission electron microscope. The ion sustained-release glass used in the present invention preferably has an amorphous structure which is a homogeneous structure, as various ions are sustained-released according to the equilibrium relationship with the ion concentration in an external environment.

The sustained release of various ions from the ion sustained-release glass used in the present invention is influenced by the particle diameter of the glass, and accordingly the particle diameter needs to be controlled by a method such as wet and/or dry grinding, classification, or screening. The particle diameter (50%) of the ion sustained-release glass used in the present invention is not particularly limited, so long as it is in the range of 0.01 µm to 100 µm. A preferable range is 0.01 µm to 50 µm, and a more preferable range is 0.1 µm to 5 p.m. The shape of the glass is not particularly limited, and may be any shape such as spherical, platy, crushed, and scaly. A preferable shape is spherical or crushed.

To enhance the ion sustained releasability from the ion sustained-release glass, it is preferable to surface-treat the glass surface for functionalization to increase the ion sustained releasability. Specific examples of the surface treatment material used in the surface treatment include a surface active agent, a fatty acid, an organic acid, an inorganic acid, a monomer, a polymer, each type of coupling material, a silane compound, a metal alkoxide compound, and its partial condensate. Preferably, an acid polymer and a silane compound are used as the surface treatment material.

An example of the method of surface-treating the ion sustained-release glass using an acid polymer and a silane compound as the surface treatment material, in detail, the method of coating the surface of the ion sustained-release glass with a silane compound and then surface-treating the ion sustained-release glass using an acid polymer, is described below.

A silane compound expressed by general formula (I)

[Chemical Formula 1]

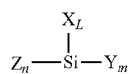

(in the formula, Z is RO—, X is halogen, Y is OH—, R is an organic group whose carbon number is less than or equal to 8, and n, m, and L are each an integer from 0 to 4 where n+m+L=4) is mixed in an aqueous dispersion containing ion sustained-release glass finely grinded into a desired average particle diameter by grinding or the like. The mixture is hydrolyzed or partially hydrolyzed in the system to generate a silanol compound, which is then condensed and forms a coating on the surface of the ion sustained-release glass.

In the above-mentioned polysiloxane treatment method, the hydrolysis and condensation of the silane compound and the polysiloxane treatment on the glass surface are simultaneously performed in the same system. Alternatively, a polysiloxane coating can also be formed efficiently on the surface of the ion sustained-release glass by a surface treatment method of performing the hydrolysis and condensation of the silane compound in another system to generate a low condensate silane compound (oligomer) and mixing it in an aqueous dispersion containing ion sustained-release glass. A more preferable method is polysiloxane treatment in which mixture is performed using a commercially-available low condensate silane compound (oligomer) without a low condensate generation process. This method is preferable for the following reason. In the case where a silane compound monomer is used, condensation occurs three-dimensionally and self-condensation is dominant due to the presence of a large amount of water in the polysiloxane treatment process, making it impossible to form a uniform polysiloxane coating on the glass surface.

In the case where a low condensate silane compound (oligomer) is used, on the other hand, a polysiloxane coating can be uniformly formed on the glass surface for each unit that has a polysiloxane main chain of a certain length. The shape of the low condensate silane compound (oligomer) is not particularly limited, though a straight chain is more preferable than a three-dimensional body. The degree of polymerization is preferably in the range of 2 to 20 and more preferably in the range of 2 to 6, given that a greater length causes lower condensation reactivity and results in poor polysiloxane coating formation on the surface of the ion sustained-release glass. The molecular weight in this case is in the range of 500 to 600.

The polysiloxane treatment in the aqueous dispersion is performed in a relatively low-speed stirring state. The temperature is in the range of ambient temperature to 100° C., and preferably in the range of ambient temperature to 50° C. The stirring time is typically in the range of several minutes to several tens of hours, and preferably in the range of 30 minutes to 4 hours. No special method is required for stirring, which can be conducted with a facility typically used in the industry. For example, a stirrer capable of stirring slurry forms, such as a universal mixing stirrer or a planetary mixer, may be used. The stirring temperature may be any temperature at which an aqueous medium does not volatilize, i.e. any temperature less than the boiling point of the aqueous medium. The stirring time needs to be adjusted because the speed of gelation by condensation is influenced by the type or addition amount of the silane compound or low condensate silane compound, the type or particle diameter of the glass and its proportion in the aqueous dispersion, and the type of the aqueous medium or its proportion in the aqueous dispersion. Besides, stirring needs to be performed until the gel is formed. Since excessively fast stirring breaks the gel structure and hinders uniform coating formation, the stirring speed needs to be low.

The aqueous medium is composed of water and alcohol. The addition of alcohol has a significantly advantageous effect of reducing the aggregability of the ion sustained-release glass filler during drying and improving its cracking property. The alcohol is preferably an alcohol whose carbon number is 2 to 10. In the case where an alcohol whose carbon number exceeds 10 is added, a long time is required to dry and remove the solvent due to high boiling point. Specific alcohols include ethyl alcohol, n-propyl alcohol, isopropyl alcohol, n-butyl alcohol, t-butyl alcohol, isobutyl alcohol, n-pentyl alcohol, isoamyl alcohol, n-hexyl alcohol, n-heptyl alcohol, n-octyl alcohol, and n-dodecyl alcohol. An alcohol whose carbon number is 2 to 4, such as ethyl alcohol, n-propyl alcohol, or isopropyl alcohol, is preferably used. The addition amount of the alcohol is 5 to 100 parts by weight and preferably 5 to 20 parts by weight, with respect to water. The addition amount exceeding 100 parts by weight causes problems such as complicating the drying step. The glass content is in the range of 25 to 100 parts by weight and preferably in the range of 30 to 75 parts by weight, with respect to the aqueous medium. In the case where the content exceeds 100 parts by weight, the speed of gelation by condensation is high, and a uniform polysiloxane coating layer is difficult to be formed. In the case where the content is less than 25 parts by weight, the glass settles out in the stirring state or phase separation occurs in the aqueous medium. The addition amount of the silane compound depends on the particle diameter of the glass. The addition amount of the silane compound is in the range of 0.1 to 10 parts by weight and preferably in the range of 0.1 to 4 parts by weight in terms of SiO2, with respect to the glass. In the case where the addition amount is less than 0.1 parts by weight, an aggregate results as crushing into primary particles is impossible, with there being no polysiloxane coating layer formation effect. In the case where the addition amount exceeds 10 parts by weight, the solidified matter after drying is too hard to be crushed.

The system which is in a "gel" state is dried, has the aqueous medium removed, and solidified. The drying is made up of two steps that are maturation and firing. Maturation is intended to grow the gel structure and remove the aqueous medium, and firing is intended to strengthen the gel structure. Maturation needs to be performed in a static state to keep the gel structure from distortion and remove the aqueous medium, and a facility such as a box-type hot air dryer is preferably used. The maturing temperature is in the range of ambient temperature to 100° C., and preferably in the range of 40° C. to 80° C. In the case where the temperature is below this range, the aqueous medium cannot be removed sufficiently. In the case where the temperature is above this range, rapid volatilization occurs, and the gel structure may become defective or peel away from the glass surface. The maturing time depends on the capacity of the drier or the like, and may be any time sufficient to remove the aqueous medium.

The firing step includes temperature rise and mooring. Temperature rise is preferably performed gradually over a long time until a target temperature is reached. Rapid temperature rise causes poor heat conduction of the gel dispersion, as a result of which a crack may occur in the gel structure. Mooring is firing at a constant temperature. The firing temperature is in the range of 100° C. to 350° C., and preferably in the range of 100° C. to 200° C.

As described above, the aqueous medium is removed from the gel by drying, and a contracted solidified matter is obtained. The solidified matter is in an ion sustained-release glass aggregate state. The solidified matter, however, is not simply an aggregate of ion sustained-release glass, but polysiloxane formed by condensation is present on the boundary surfaces of individual fine particles. Accordingly, when the solidified matter is crushed into a size equivalent to the ion sustained-release glass before the polysiloxane treatment in the next step, the ion sustained-release glass whose surface is coated with polysiloxane is obtained. Here, "crushing into a size equivalent to the ion sustained-release glass before the polysiloxane treatment" means crushing into primary particles of ion sustained-release glass coated with polysiloxane. The difference from the original ion sustained-release glass lies in that the individual fine particles are coated with polysiloxane. The inclusion of a secondary aggregate is, however, allowed to an extent that causes no problem. The solidified matter can be easily crushed by applying a shearing force or an impact force. For example, a Henschel mixer, a cross rotary mixer, a super mixer, or the like may be used for crushing.

Examples of the silane compound expressed by general formula (I) include tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, and silicon hydroxide (silicon oxide hydrate). Tetramethoxysilane and tetraethoxysilane are particularly preferable. An aggregate represented by the silane compound expressed by general formula (I) is more preferable.

A low condensate of the silane compound expressed by general formula (I) is more preferable. An example of this is a low condensate silane compound obtained by partially hydrolyzing tetramethoxysilane and tetraethoxysilane and condensing them. These compounds may be used singly or in combination.

An organo silane compound may be added as part of the silane compound expressed by general formula (I) during polysiloxane treatment. Specific examples of the organosilane compound include methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloxypropyltrimethoxysilane, γ-glycidoxypropylmethoxysilane, γ-mercaptopropyltrimethoxysilane, γ-aminopropyltriethoxysilane, 3-aminopropyltriethoxysilane, methyltrichlorosilane, and phenyltrichlorosilane. Methyltrimethoxysilane, ethyltrimethoxysilane, vinyltriethoxysilane, and phenyltrichlorosilane are particularly preferable. These compounds may be used singly or in combination. In such a compound, however, an organic group is present in the polysiloxane layer, and so there is a possibility that distortion occurs during polysiloxane layer formation and a problem with mechanical strength results. Therefore, the addition of the compound needs to be limited to a small amount. Moreover, an alkoxide compound, halide, hydrated oxide, nitrate, or carbonate of another metal may be added as part of the silane compound expressed by general formula (I) during polysiloxane treatment.

The ion sustained-release glass coated with polysiloxane in the above-mentioned step undergoes an acid polymer treatment of reacting with an acid polymer, as a result of which the most preferable surface-treated ion sustained-release glass according to the present invention is obtained. The acid polymer treatment may employ a facility typically used in the industry, so long as it is a dry flow stirrer. Examples of such a facility include a Henschel mixer, a super mixer, and a high speed mixer. The reaction of the ion sustained-release glass, on which the polysiloxane coating is formed, with the acid polymer can be made by contacting the ion sustained-release glass with an acid polymer solution by impregnation, spray, or the like. As an example, the polysiloxane-coated ion sustained-release glass is caused to dry flow and, in the flow state, the acid polymer solution is dispersed from above and sufficiently stirred. The method of dispersing the acid polymer solution is not particularly limited, though dropping or spray that enables uniform dispersion is preferable. The reaction is preferably conducted around ambient temperature. If the temperature is high, the reaction between the acid reactive element and the acid polymer accelerates and the acid polymer phase formation is not uniform. After heat treatment, the heat-treated object can be easily crushed by applying a shearing force or an impact force. The crushing may be performed with, for example, the facility used in the above-mentioned reaction.

A solvent employed for preparing the acid polymer solution used in the reaction may be any solvent for dissolving the acid polymer. Examples of the solvent include water, ethanol, and acetone. Of these, water is particularly preferable. When water is used, an acid group of the acid polymer dissociates and reacts uniformly with the surface of the ion sustained-release glass.

The weight average molecular weight of the polymer dissolved in the acid polymer solution is in the range of 2000 to 50000, and preferably in the range of 5000 to 40000. Surface-treated ion sustained-release glass treated with an acid polymer whose weight-average molecular weight is less than 2000 tends to have low ion sustained releasability. An acid polymer whose weight-average molecular weight exceeds 5000 increases the viscosity of the acid polymer solution, and makes it difficult to perform acid polymer treatment. The acid polymer concentration in the acid polymer solution is preferably in the range of 3% to 25% by weight, and more preferably in the range of 8% to 20% by weight. In the case where the acid polymer concentration is less than 3% by weight, the above-mentioned acid polymer phase is weak. In the case where the acid polymer concentration exceeds 25% by weight, the polysiloxane layer (porous) is difficult to be diffused. Besides, problems such as the following arise: the acid-base reaction accelerates upon contact with the ion sustained-release glass, and hardening begins during the reaction and condensation occurs. The addition amount of the acid polymer solution to the polysiloxane-coated ion sustained-release glass is preferably in the range of 6% to 40% by weight, and more preferably in the range of 10% to 30% by weight. Converting this addition amount, an optimal amount of the acid polymer with respect to the polysiloxane-coated ion sustained-release glass is in the range of 1% to 7% by weight, and an optimal amount of water is in the range of 10% to 25% by weight.

The acid polymer that can be used to form the acid polymer reaction phase on the surface of the polysiloxane-coated ion sustained-release glass by the method described above is a copolymer or a homopolymer of a polymerizable monomer having an acid group such as a phosphoric acid residue, a pyrophosphoric acid residue, a thiophosphoric acid residue, a carboxylic acid residue, or a sulfonic acid group. Examples of the polymerizable monomer include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, 4-(meth)acryloyloxyethoxycarbonylphthalic acid, 4-(meth) acryloyloxyethoxycarbonylphthalic anhydride, 5-(meth) acryloylaminopentylcarboxylic acid, 11-(meth)acryloyloxy-1,1-undecanedicarboxylic acid, 2-(meth) acryloyloxyethyldihydrogenphosphate, 10-(meth) acryloyloxydecyldihydrogenphosphate, 20-(meth) acryloyloxyeicosyldihydrogenphosphate, 1,3-di(meth) acryloyloxypropyl-2-dihydrogenphosphate, 2-(meth) acryloyloxyethylphenyl phosphoric acid, 2-(meth) acryloyloxyethyl-2'-bromoethyl phosphoric acid, (meth) acryloyloxyethylphenylphosphonate, di(2-(meth) acryloyloxyethyl)pyrophosphate, 2-(meth) acryloyloxyethyldihydrogendithiophosphate, and 10-(meth)acryloyloxydecyldihydrogenthiophosphate. Of these polymers, a homopolymer or a copolymer of α-β unsaturated carboxylic acid that is relatively slow in acid-base reaction with an acid reactive element is preferable. An acrylic acid polymer, an acrylic acid-maleic acid copolymer, and an acrylic acid-itaconic acid copolymer are more preferable.

The ion sustained-release glass used in the present invention has a feature of continuously sustained-releasing an ion species resulting from the glass composition, and is different from temporary release of a large amount by dissolution of a metal fluoride or the like in water.

Whether or not the ion sustained-release glass or another filler has ion sustained releasability can be determined by the following method.

0.1 g of the ion sustained-release glass or another filler is added to 100 g of distilled water. The ion sustained-release glass or another filler can be regarded as having ion sustained releasability in the case where the ion concentration (F1) or the element concentration (F1) attributable to the ion species sustain-released in the distilled water when stirred for 1 hour and the ion concentration (F2) or the element concentration (F2) attributable to the ion species sustain-released in the distilled water when stirred for 2 hours satisfy the relationship of the following Expression (1):

$$F2>F1 \qquad \text{Expression (1).}$$

If a plurality of types of ions are sustained-released from the ion sustained-release glass, the ion concentrations or element concentrations of all types of ions do not necessarily need to satisfy Expression (1). The ion sustained-release glass may be regarded as having ion sustained releasability in the case where the ion concentration or element concentration of at least one type of ion satisfies Expression (1).

The ion sustained-release glass used in the present invention preferably has an acid neutralizing capacity attributable to the ion sustained release effect. The acid neutralizing capacity can be checked by adding 0.1 g of the ion sustained-release glass to 10 g of a lactic acid water solution with pH adjusted to 4.0, and measuring the pH change when stirred for 5 minutes. The ion sustained-release glass can be regarded as having an acid neutralizing capacity in the case where the pH is greater than or equal to 5.5, more preferably greater than or equal to 6.0, and most preferably greater than or equal to 6.5.

The content of the filling material (b) is preferably in the range of 3% to 21% by weight and more preferably in the range of 3% to 18% by weight, with respect to the total weight of the dental resin temporary sealing material. In the case where the content of the filling material is less than 3% by weight, the content of the noncrosslinked (meth)acrylate polymer is high. This accelerates penetration and swelling of the monofunctional (meth)acrylate polymerizable monomer, the hydrophilic polymerizable monomer, and the like, and makes it impossible to ensure a sufficient operation time. Besides, the operability for reproducing the anatomical form during filling to the cavity decreases, and the sealability is adversely affected such as the hardened material being deformed or falling off due to mastication or the like. In the case where the content of the filling material exceeds 21% by weight, the content of the noncrosslinked (meth)acrylate polymer in the dental resin temporary sealing material is low. This hinders uniform penetration and swelling of the monofunctional (meth)acrylate polymerizable monomer, hydrophilic polymerizable monomer, and the like, leading to problems in material property, sealability, removability, etc.

The monofunctional (meth)acrylate polymerizable monomer (c) may be any (meth)acrylate polymerizable monomer having a well-known monofunctional acryloyl group and/or methacryloyl group typically used in the dental field, so long as it is other than the below-mentioned hydrophilic polymerizable monomer (d). The monofunctional (meth)acrylate polymerizable monomer in the present invention inclusively means both an acryloyl group-containing polymerizable monomer and a methacryloyl group-containing polymerizable monomer.

Specific examples of the monofunctional (meth)acrylate polymerizable monomer are as follows.

Examples of the monofunctional (meth)acrylate polymerizable monomer include: (meth)acrylic esters such as methyl (meth)acrylate, ethyl (meth)acrylate, butyl (meth)acrylate, hexyl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, glycerol (meth)acrylate, and isobonyl (meth)acrylate; silane compounds such as γ-(meth)acryloyloxypropyltrimethoxysilane and γ-(meth)acryloyloxypropyltriethoxysilane; and nitrogen-containing compounds such as 2-(N,N-dimethylamino)ethyl(meth)acrylate and N-methylol (meth)acrylamide.

The content of the monofunctional (meth)acrylate polymerizable monomer is not limited so long as it is in the range of 4% to 16% by weight. In the case where the content of the monofunctional (meth)acrylate polymerizable monomer is less than 4% by weight, the hardenability of the resin component decreases, causing a problem in material property of the hardened material. In the case where the content of the monofunctional (meth)acrylate polymerizable monomer exceeds 16% by weight, the polymerization shrinkage of the resin component is significant, causing a problem such as a decrease in cavity sealability.

The hydrophilic polymerizable monomer (d) is not limited, so long as it has at least one polymerizable group and at least 5 parts by weight dissolve in 100 parts by weight water at 23° C.

In the present invention, the hydrophilicity is evaluated by the following method.

100 g of distilled water is put in a sample bottle, and 5 g of the polymerizable monomer is added to it and mixed to be uniform. The sample is then left for 24 hours. The solubility is regarded as greater than or equal to 5% in the case where the distilled water and the polymerizable monomer are colorless and transparent, and less than or equal to 5% in the case where the distilled water and the polymerizable monomer are white.

Specific examples of the hydrophilic polymerizable monomer include 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2-hydroxypropyl-1,3-di(meth)acrylate, 3-hydroxypropyl-1,2-di(meth)acrylate, pentaerythritol di(meth)acrylate, 2-trimethylammoniumethyl (meth)acrylchloride, (meth)acrylamide, 2-hydroxyethyl (meth)acrylamide, and polyethylene glycol di(meth)acrylate (the number of oxyethylene groups is greater than or equal to 9), though the hydrophilic polymerizable monomer is not limited to such.

These hydrophilic polymerizable monomers may be used singly or in combination. Of these hydrophilic polymerizable monomers, a hydrophilic polymerizable monomer that dissolves by 10 parts by weight or more in 100 parts by weight water at 23° C. is preferable, and a hydrophilic polymerizable monomer that dissolves by 20 parts by weight or more in 100 parts by weight water at 23° C. is more preferable. Specific examples of the hydrophilic polymerizable monomer include 2-hydroxyethyl (meth)acrylate, polyethylene glycol di(meth)acrylate (the number of oxyethylene groups is 9), polyethylene glycol di(meth)acrylate (the number of oxyethylene groups is 14), and polyethylene glycol di(meth)acrylate (the number of oxyethylene groups is 23), though the hydrophilic polymerizable monomer is not limited to such.

To enable the dental resin temporary sealing material composition according to the present invention to exhibit excellent sealability to cavity walls after hardening, flexible material property, low water absorbability, stable hardness by water immersion, little dimensional change, and the like, the inclusion of a hydrophilic polymerizable monomer having at least two polymerizable groups is preferable, and the inclusion of both a hydrophilic polymerizable monomer having one polymerizable group and a hydrophilic polymerizable monomer having at least two polymerizable groups is more preferable.

The content of the hydrophilic polymerizable monomer is not limited so long as it is in the range of 4% to 13% by weight. A preferable range is 6% to 13% by weight.

In the case where the content of the hydrophilic polymerizable monomer is less than 4% by weight, the affinity for the cavity walls which are hydrophilic is poor, leading to a decrease in cavity sealability. In the case where the content of the hydrophilic polymerizable monomer exceeds 13% by weight, the polymerization hardenability of the resin component is low, causing problems such as an increased water absorption rate and significant dimensional change.

A polymerization initiator that can be used in the dental resin temporary sealing material composition according to the present invention is not particularly limited, and a well-known radical precursor used in the dental field may be used without limitation. Typically, polymerization initiators are mainly classified into a type (photopolymerization initiator) that initiates polymerization by light irradiation and a type (chemical polymerization initiator) that initiates polymerization by mixture immediately before use, and preferably used.

The photopolymerization initiator may be a photosensitizer, or a combination of a photosensitizer and a photopolymerization promoter, though not limited to such.

Specific examples of the photosensitizer include: α-diketones such as benzyl, camphorquinone, α-naphthyl, acetonaphthene, p,p'-dimethoxybenzyl, p,p'-dichlorobenzylacetyl, pentanedione, 1,2-phenanthrenequinone, 1,4-phenanthrenequinone, 3,4-phenanthrenequinone, 9,10-phenanthrenequinone, and naphthoquinone; benzoin alkylethers such as benzoin, benzoin methyl ether, and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone; benzophenones such as benzophenone, p-chlorobenzophenone, and p-methoxybenzophenone; acylphosphine oxides such as 2,4,6-trimethylbenzoyl-diphenylphosphine oxide, and bis(2,6-dimethoxybenzoyl)-2,4,4-trimethylpentylphosphine oxide; α-aminoacetophenones such as 2-benzyl-dimethylamino-1-(4-morpholinophenyl)-butanone-1 and 2-benzyl-diethylamino-1-(4-morpholinophenyl)-propanone-1; ketals such as benzyl dimethyl ketal, benzyl diethyl ketal, and benzyl(2-methoxyethyl ketal); and titanocenes such as bis(cyclopentadienyl)-bis[2,6-difluoro-3-(1-pyrrolyl)phenyl]-titanium, bis(cycpentadienyl)-bis (pentanefluorophenyl)-titanium, and bis(cyclopentadienyl)-bis(2,3,5,6-tetrafluoro-4-disiloxyphenyl)-titanium.

Specific examples of the photopolymerization promoter include: tertiary amines such as N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranylic acid methyl ester, N,N-dihydroxyethylaniline, p-N,N-dihydroxyethyl-toluidine, p-dimethylaminophenyl alcohol, p-dimethylaminostylene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)diethanol; secondary amines such as N-phenylglycine; barbituric acids such as 5-butylbarbituric acid, and 1-benzyl-5-phenylbarbituric acid; tin compounds such as dibutyltin diacetate, dibutyltin dilaurate, dioctyltin dilaurate, dioctyltin diverthatate, dioctyltinbis(mercaptoacetic acid isooctyl ester) salt, and tetramethyl-1,3-diacetoxydistannoxane; aldehyde compounds such as lauryl aldehyde and terephthalaldehyde; and sulfur-containing compounds such as dodecyl mercaptan, 2-mercaptobenzoxazole, 1-decanethiol, and thiosalicylic acid.

For improved photopolymerization promoting ability, it is effective to add, in addition to the above-mentioned photopolymerization promoter, oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid, and dimethylol propionic acid.

The chemical polymerization initiator may be a redox type polymerization initiator system composed of an organic peroxide/amine compound, an organic peroxide/amine compound/sulfinate, or an organic peroxide/amine compound/borate compound, or an organic metal type polymerization initiator system that reacts with oxygen or water to initiate polymerization. The sulfinate or the borate compound can further initiate polymerization by reacting with a polymerizable monomer having an acidic group, though the present invention is not limited to such.

Specific examples of the organic peroxide include benzoyl peroxide, p-chlorobenzoyl peroxide, 2,4-dichlorobenzoyl peroxide, acetyl peroxide, lauroyl peroxide, tertiary butyl peroxide, cumene hydroperoxide, 2,5-dimethyl-2,5-di(benzoylperoxy)hexane, 2,5-dihydroperoxide, methyl ethyl ketone peroxide, and tertiary butyl peroxybenzoate.

The amine compound is preferably a secondary amine or a tertiary amine in which an amine group is attached to an aryl group, as an example. Specific examples include p-N,N-dimethyl-toluidine, N,N-dimethyl aniline, N-β-hydroxyethyl-aniline, N,N-di(β-hydroxyethyl)-aniline, p-N,N-di(β-hydroxyethyl)-toluidine, N-methyl-aniline, and p-N-methyl-toluidine.

Specific examples of the sulfinate include benzenesulfinic sodium, benzenesulfinic lithium, and p-toluenesulfinic sodium.

Specific examples of the borate compound include sodium salt, lithium salt, potassium salt, magnesium salt, tetrabutylammonium salt, and tetramethylammonium salt of trialkylphenyl boron, trialkyl(p-fluorophenyl) boron (alkyl group is n-butyl group, n-octyl group, n-dodecyl group, etc.), and the like.

Specific examples of the organic metal type polymerization initiator include organic boron compounds such as triphenylborane, tributylborane, and tributylborane partial oxide.

As a thermal polymerization initiator by heating or warming, not only the above-mentioned organic peroxide but also an azo compound such as azobisisobutyronitrile, azobisisobutyric acid methyl, or azobiscyanovaleric acid is preferably used.

These polymerization initiators may be used singly or in combination, regardless of the polymerization mode or the polymerization method. The polymerization initiator may be subject to a secondary treatment such as microencapsulation, to stabilize polymerization or delay polymerization.

Of these polymerization initiators, the chemical polymerization initiator that initiates polymerization by mixture immediately before use is preferably used. The use of the chemical polymerization initiator is most desirable for its simplicity. Of the chemical polymerization initiators, a combination of an organic peroxide and a tertiary amine is more preferable, and a combination such as an aromatic amine in which an amino group such as p-N,N-dimethyl aminobenzoic acid ethyl and benzoyl peroxide are directly attached to a benzene ring or an aliphatic amine that has a double bond in a molecule of N,N-dimethylaminoethylmethacrylate or the like is most preferable.

The content of the polymerization initiator can be appropriately selected depending on use. A preferable range is 0.1 to 5 parts by weight, and a more preferable range is 0.1 to 2 parts by weight. In the case where the content of the polymerization initiator is less than 0.1 parts by weight, the polymerization hardenability is insufficient, and the desired material property or performance cannot be achieved. In the case where the content of the polymerization initiator exceeds 5 parts by weight, the polymerization hardening accelerates, which causes a problem with operability such as the difficulty of the filling operation to the cavity. Besides, the hardened material becomes harder with polymerization, which causes a problem with removability such as the difficulty of removing the hardened material from the cavity upon removal.

The plasticizer (f) is not particularly limited, and any well-known plasticizer may be used without limitation. Specific examples of the plasticizer include: phthalate esters such as dimethyl phthalate, diethyl phthalate, dibutyl phthalate, diheptyl phthalate, dioctyl phthalate, di-isodecyl phthalate, butyl benzyl phthalate, diisononyl phthalate, ethyl phthalyl ethyl glycolate, and butyl phthalyl butyl glycolate; dibasic acid esters other than phthalic acid, such as dibutyl adipate, dibutyl diglycol adipate, dibutyl sebacate, dioctyl sebacate, dibutyl maleate, and dibutyl fumarate; glycerol esters such as glycerol triacetate; phosphate esters such as tributyl phosphate, trioctyl phosphate, and triphenyl phosphate; and carboxylate esters such as benzyl benzoate, ethyl benzoate, butyl benzoate, and amyl benzoate, though the plasticizer is not limited to such. These plasticizers may be used singly or in combination. Of these plasticizers, carboxylate esters are preferable, and benzyl benzoate, ethyl benzoate, butyl benzoate, and amyl benzoate are particularly preferable.

The content of the plasticizer can be appropriately adjusted depending on the use method, the purpose of use, the composition, etc. The content of the plasticizer is not limited so long as it is in the range of 5% to 25% by weight.

A preferable range is 8% to 25% by weight. In the case where the content of the plasticizer is less than 5% by weight, the hardened material lacks flexibility, which causes a problem such as a failure to remove the hardened material at once upon removal. In the case where the content of the plasticizer exceeds 25% by weight, the plasticizer flows out over time after temporary sealing, and so a dimensional change occurs. This may lead to lower sealability of the cavity.

In addition to the components (a) to (f) described above, the following components may be optionally added to the dental resin temporary sealing material composition according to the present invention depending on need: a polymerizable monomer having two or more non-hydrophilic functional groups as a cross linker, a vehicle such as fumed silica, an ultraviolet absorber such as 2-hydroxy-4-methylbenzophenone, a polymerization inhibitor such as hydroquinone, hydroquinone monomethyl ether, or 2,5-ditertiary butyl-4-methylphenol, an antitarnish agent, an antimicrobial, a color pigment, and other conventionally known additives.

The package form of the dental resin temporary sealing material composition according to the present invention is not particularly limited, and any package form such as powder-liquid, powder-paste, paste-liquid, paste-paste, and one paste may be used. A preferable package form is powder-liquid or powder-paste.

INDUSTRIAL APPLICABILITY

The dental resin temporary sealing material composition according to the present invention relates to a temporary sealing material used in dental treatment, and is an industrially applicable invention.

EXAMPLES

Examples of the present invention and comparative examples are described in detail below, though the present invention is not limited to these examples. The following test methods are used to evaluate the performance of the dental resin temporary sealing material composition prepared in each of the examples and the comparative examples.

[Measurement of Element Content Resulting from Ion Sustained-Released from Ion Sustained-Release Glass or Filler]

0.1 g of the ion sustained-release glass or filler was added to 100 g of distilled water, and stirred for 1 hour. The element concentration resulting from each ion sustained-released in a solution filtered by an analytical syringe filter (Chromatdisk 25A, pore size: 0.2 µm, GL Sciences Inc.) is denoted by F1. Likewise, 0.1 g of the ion sustained-release glass or filler was added to 100 g of distilled water, and stirred for 2 hours. The element concentration resulting from each ion sustained-released in a solution filtered by the same operation is denoted by F2. Regarding fluorine, the fluoride ion was measured using a fluoride ion composite electrode (Model 9609, Orion Research Inc.) and an ion meter (Model 720A, Orion Research Inc.), and the measurement was used for conversion to the fluorine element concentration. Upon measurement, 0.5 ml of TISABIII (manufactured by Orion Research Inc.) was added as an ionic strength adjustor. Calibration was performed using standard solutions of 0.1 ppm, 1 ppm, 10 ppm, and 20 ppm. The other elements (Na, B, Al, Sr) were calculated by measurement, using an inductively coupled plasma atomic emission spectrophotometer (ICPS-8000, Shimadzu Corporation). Calibration was performed using standard solutions of 0 ppm, 10 ppm, 25 ppm, and 50 ppm. In the case where the measured elements were not within the calibration, the measurement was conducted with dilution according to need.

[Measurement of Element Concentration Resulting from Ion Sustained-Released from Dental Resin Temporary Sealing Material Composition]

The powder and the liquid were mixed at the ratio shown in Table 4. A stainless-steel mold (15φ×1 mm, disk-shaped) was filled with the mixture, cover glass was placed on both surfaces to apply pressure with glass mixing plates, and the mixture was hardened. After the hardening, the hardened material was taken out of the mold, and put in a plastic container containing 5 ml of distilled water. After sealed, the container was left in a constant temperature box of 37° C. for one week. After one week, the container was taken out of the constant temperature box, and the eluate from which the discoid test piece was removed was collected. The element concentration measurement was performed on the eluate by the same method as the foregoing [Measurement of element content resulting from ion sustained-released from ion sustained-release glass or filler].

[Evaluation of Acid Neutralizing Capacity of Ion Sustained-Release Glass or Filler]

The acid neutralizing capacity of the ion sustained-release glass used in the present invention was evaluated by the following method. 0.1 g of the ion sustained-release glass or filler was added to 10 g of a lactic acid water solution with pH adjusted to 4.0, and stirred for 5 minutes. The pH was then measured using a pH meter (D-51, HORIBA, Ltd.) for evaluation.

[Evaluation of Acid Neutralizing Capacity of Dental Resin Temporary Sealing Material Composition]

The powder and the liquid were mixed at the ratio shown in Table 4. A stainless-steel mold (15φ×1 mm, disk-shaped) was filled with the mixture, cover glass was placed on both surfaces to apply pressure with glass mixing plates, and the mixture was hardened. After the hardening, the hardened material was taken out of the mold, and immersed in 5 ml of a lactic acid water solution (with pH adjusted to 4.0). The pH of the lactic acid water solution after 6 hours and after 24 hours was measured using a pH meter (D-51, HORIBA, Ltd.).

[Removability]

Purpose: To evaluate the removability of the hardened material of the dental resin temporary sealing material composition.

Method: A cavity of 4.5 mm in diameter and 1.6 mm in depth was formed in a coronal portion of an extracted bovine tooth, and washed with water and dried. The powder and the liquid were mixed at the ratio shown in Table 4, and the cavity was filled with the mixture. After the temporary sealing material hardened, it was left in water of 37° C. for 24 hours. Each of five dentists then conducted the operation of removing the hardened material (five samples) using a probe, and evaluated the removability on the following 4-point scale. The most frequent grade was set as the result of evaluation of the removability.

A: The material is easily removable as a block.

B: The material is easily removable with no residue on the tooth surface, though not removed as a block.

C: The material is torn during removal, and remains on the tooth surface.

D: The material is hard and is difficult to be removed.

[Sealability]

Purpose: To evaluate the sealability of the hardened material of the dental resin temporary sealing material composition.

Method: A cavity of 4.5 mm in diameter and 1.6 mm in depth was formed in a coronal portion of an extracted bovine tooth, and washed with water and dried. The powder and the liquid were mixed at the ratio shown in Table 4, and the cavity was filled with the mixture. After the temporary sealing material hardened, it was left in water of 37° C. for 24 hours. A thermal cycle of immersion in water of 4° C. and 60° C. each for 1 minute was repeatedly performed 50 times. After the thermal cycle ends, the tooth was immersed in a 0.1% basic fuchsin water solution for 2 hours. The filled sample was then removed, and the pigment invasion state was observed. The evaluation was made on the following 4-point scale. Five samples were tested, and the most frequent grade is shown.

A: No pigment penetration.
B: Penetration up to inside enamel.
C: Penetration up to inside dentin.
D: Penetration throughout the cavity.

[Measurement of Shore D Hardness]

Purpose: To evaluate the hardness of the hardened material of the dental resin temporary sealing material composition.

Method: The powder and the liquid were mixed at the ratio shown in Table 4. A stainless-steel mold (15φ×1 mm, disk-shaped) was filled with the mixture, cover glass was placed on both surfaces to apply pressure with glass mixing plates, and the mixture was hardened. After the hardening, the hardened material was taken out of the mold, and put in a plastic container containing ion-exchange water. After sealed, the container was left in a constant temperature box of 37° C. for one week. After one week, the container was taken out of the constant temperature box, and the measurement was performed using a Shore D hardness tester. Five samples produced were each subject to the measurement three times, and the average of all measurements is shown. The measurement conforms to JIS K6253 (vulcanized rubber test method). The Shore D hardness is preferably in the range of 30 to 50. In the case where the Shore D hardness is less than 30, deformation due to biting pressure is likely to occur. In the case where the Shore D hardness exceeds 50, problems such as the difficulty of removal due to hardness arise.

The following shows the names and abbreviations of the components used in the examples of the present invention and the comparative examples.

(a: Noncrosslinked (Meth)Acrylate Polymer)
PEMA1: polyethyl methacrylate (50% average particle diameter: 70 μm, weight-average molecular weight: 950000, shape: spherical)
PMMA1: polymethyl methacrylate (50% average particle diameter: 80 μm, weight-average molecular weight: 1000000, shape: spherical)
PEMA2: polyethyl methacrylate (50% average particle diameter: 4 μm, weight-average molecular weight: 40000, shape: spherical)
PMMA2: polymethyl methacrylate (50% average particle diameter: 160 μm, weight-average molecular weight: 1600000, shape: spherical)

(b: Filling Material)
Ion sustained-release glass 1
Ion sustained-release glass 2
Ion sustained-release glass 3
Filler 1: sodium fluoride powder (Nacalai Tesque, Inc.)

(c: Monofunctional (Meth)Acrylate Polymerizable Monomer)
MMA: methyl methacrylate (d: Hydrophilic Polymerizable Monomer)
HEMA: 2-hydroxyethyl methacrylate
14EG: polyethylene glycol dimethacrylate (number of cycles: 14)

(e: Polymerization Initiator)
BPO: benzoyl peroxide
DMPT: N,N-dimethyl p-toluidine (f: Plasticizer)
BB: benzyl benzoate
Hydrophilic polymerizable monomer
3G: triethyleneglycol dimethacrylate

[Manufacture of Ion Sustained-Release Glass 1]

The raw materials that are silicon dioxide, aluminum oxide, boron oxide, sodium fluoride, and strontium carbonate (glass composition: $SiO_2$ 23.8% by mass, $Al_2O_3$ 16.2% by mass, $B_2O_3$ 10.5% by mass, SrO 35.6% by mass, $Na_2O$ 2.3% by mass, F 11.6% by mass) were uniformly mixed using a ball mill to prepare the raw material mixture, and the raw material mixture was molten in a melting furnace at 1400° C. The melt was then taken out of the melting furnace, and cooled on a cool steel plate, a roll, or in water to create glass. After introducing 4 kg of alumina pebbles of 6 mmφ in diameter into an alumina pot (internal volume: 3.6 liters) of a four-tier vibration mill, 500 g of the glass obtained above was introduced and grinded for 40 hours, thus obtaining the ion sustained-release glass filler 1. The 50% average particle diameter of the ion sustained-release glass filler 1 measured by a laser diffraction particle size measuring instrument (microtrack SPA, Nikkiso Co., Ltd.) was 1.2 μm. The element content resulting from the ion released from the ion sustained-release glass 1 was measured and its consistency with Expression (1) was determined. The result is shown in Table 1.

[Manufacture of Ion Sustained-Release Glass 2]

The following polysiloxane treatment and acid polymer treatment were performed to obtain the surface-treated ion sustained-release glass 2.

500 g of the above-mentioned ion sustained-release glass 1 and a silane compound (a low condensate of a silane compound obtained by stirring 5 g of tetramethoxysilane, 1000 g of water, and 100 g of ethanol for 2 hours at ambient temperature beforehand) were cast into a universal mixing stirrer and stirred and mixed for 90 minutes. The mixture was then heat-treated at 140° C. for 30 hours, thus obtaining the heat-treated object. The heat-treated object was crushed using a Henschel mixer, to obtain polysiloxane-coated glass. While stirring 500 g of the polysiloxane-coated ion sustained-release glass, an acid polymer water solution (polyacrylic acid water solution, polymer concentration: 13% by weight, weight-average molecular weight: 20000, Nacalai Tesque, Inc.) was sprayed using a Henschel mixer. Heat treatment (at 100° C. for 3 hours) was then performed to manufacture the surface-treated ion sustained-release glass 2. The 50% average particle diameter of the ion sustained-release glass 2 measured by a laser diffraction particle size measuring instrument (microtrack SPA: Nikkiso Co., Ltd.) was 1.3 μm. The element content resulting from the ion released from the surface-treated ion sustained-release glass 2 was measured and its consistency with Expression (1) was determined. The result is shown in Table 1.

[Manufacture of Ion Sustained-Release Glass 3]

The raw materials that are silicon dioxide, aluminum oxide, boron oxide, sodium fluoride, and strontium carbonate were mixed, and the mixture was molten at 1400° C. to obtain glass (glass composition: $SiO_2$ 19.8% by mass, $Al_2O_3$ 19.8% by mass, $B_2O_3$ 11.7% by mass, SrO 35.0% by mass, $Na_2O$ 2.3% by mass, F 11.4% by mass). The glass was then grinded for 10 hours using a vibration mill, thus obtaining the glass 3. 500 g of the glass 3 and a silane compound (a low condensate of a silane compound obtained by stirring 10 g of tetramethoxysilane, 1500 g of water, 100 g of ethanol, 70 g of methanol, and 50 g of isopropanol for 2 hours at ambient temperature beforehand) were cast into a universal mixing stirrer and stirred and mixed for 90 minutes. The mixture was then heat-treated at 140° C. for 30 hours, thus obtaining the heat-treated object. The heat-treated object was crushed using a Henschel mixer, to obtain polysiloxane-coated ion sustained-release glass. While stirring 500 g of the polysiloxane-coated glass, an acid polymer water solution (polyacrylic acid water solution, polymer concentration: 13% by weight, weight-average molecular weight: 20000, Nacalai Tesque, Inc.) was sprayed using a Henschel mixer. Heat treatment (at 100° C. for 3 hours) was then performed to manufacture the surface-treated ion sustained-release glass 3. The 50% average particle diameter of the surface-treated ion sustained-release glass filler 3 measured by a laser diffraction particle size measuring instrument (microtrack SPA, Nikkiso Co., Ltd.) was 3.1 µm. The element content (ion content only in the case of fluoride ion) resulting from the ion released from the surface-treated ion sustained-release glass filler 3 was measured and its consistency with Expression (1) was determined. The result is shown in Table 1.

[Non-Ion Sustained-Release Filler]

The following filler was used as a non-ion sustained-release filler.

FLX: FUSELEX X (silica filler, particle diameter=2.1 µm, Tatsumori Ltd.)

SOC5: Admafine SO-C5 which is a silica filler (silica filler, average particle diameter=1.6 µm, Admatechs)

The element content resulting from the ion released from the filler was measured and its consistency with Expression (1) was determined. The result is shown in Table 1.

TABLE 1

Details of ion sustained-release glass and filler

| | | | Ion sustained-release glass | | | Non-ion sustained-release filler | |
|---|---|---|---|---|---|---|---|
| | | | Ion sustained-release glass 1 | Ion sustained-release glass 2 | Ion sustains-release glass 3 | FLX | SOC5 |
| Element concentration (ppm) | F1 | F | 8.9 | 21.3 | 15.5 | 0 | 0 |
| | | Na | 1.2 | 1.5 | 0.9 | 0 | 0 |
| | | B | 2.3 | 2.8 | 1.9 | 0 | 0 |
| | | Al | 0.2 | 0.1 | 0.1 | 0 | 0 |
| | | Sr | 9.2 | 14.6 | 9.5 | 0 | 0 |
| | F2 | F | 12.5 | 32.3 | 22.5 | 0 | 0 |
| | | Na | 1.5 | 2.3 | 1.6 | 0 | 0 |
| | | B | 2.5 | 3.7 | 3.6 | 0 | 0 |
| | | Al | 0.3 | 0.2 | 0.05 | 0 | 0 |
| | | Sr | 9.7 | 21.3 | 12.4 | 0 | 0 |
| Acid neutralizing capacity (pH) | | | 6.6 | 6.8 | 6.8 | 4.1 | 4.1 |
| Consistency with F2 > F1 (Expression 1) | | | Consistent | Consistent | Consistent | Not consistent | Not consistent |

0.1 g of the ion sustained-release glass or filler was added to 10 g of a lactic acid water solution with pH adjusted to 4.0, and stirred for 5 minutes. The following results were then obtained. The pH of the ion sustained-release glass was greater than or equal to 6.5, indicating that the ion sustained-release glass has the acid neutralizing capacity. The pH of the non-ion sustained-release filler was, on the other hand, almost unchanged at 4.1, indicating that the non-ion sustained-release filler does not have the acid neutralizing capacity. Moreover, the element content (ion content only in the case of fluoride ion) sustained-released from the ion sustained-release glass was consistent with Expression (1), whereas the element content (ion content only in the case of fluoride ion) sustained-released from the non-ion sustained-release filler was not consistent with Expression (1).

TABLE 2

Powder composition (g)

| Powder No. | (a) Component | | | | (b) Component | | | Filler 1 | (e) Component BPO |
|---|---|---|---|---|---|---|---|---|---|
| | PEMA1 | PEMA2 | PMMA1 | PMMA2 | Ion sustained-release glass 1 | Ion sustained-release glass 2 | Ion sustained-release glass 3 | | |
| P1 | — | — | 93 | — | 6.5 | — | — | — | 0.5 |
| P2 | 70 | — | — | — | — | 29.5 | — | — | 0.5 |

TABLE 2-continued

| | Powder composition (g) | | | | | | | | |
|---|---|---|---|---|---|---|---|---|---|
| | (a) Component | | | | (b) Component | | | | (e) Component |
| Powder No. | PEMA1 | PEMA2 | PMMA1 | PMMA2 | Ion sustained-release glass 1 | Ion sustained-release glass 2 | Ion sustained-release glass 3 | Filler 1 | BPO |
| P3 | — | — | 98 | — | 1.5 | — | — | — | 0.5 |
| P4 | 63.5 | — | — | — | — | 36 | — | — | 0.5 |
| P5 | 85 | — | — | — | — | 14.5 | — | — | 0.5 |
| P6 | — | — | 85 | — | — | — | 14.5 | — | 0.5 |
| P7 | — | — | 85 | — | — | — | — | 14.5 | 0.5 |
| P8 | 85 | — | — | — | — | — | 10 | 4.5 | 0.5 |
| P9 | — | 80 | — | — | 19.5 | — | — | — | 0.5 |
| P10 | — | — | — | 80 | — | 19.5 | — | — | 0.5 |

TABLE 3

| | Liquid composition (g) | | | | | |
|---|---|---|---|---|---|---|
| | (c) Component | (f) Component | (d) Component | | Non-hydrophilic polymerizable monomer | (e) Component |
| Liquid No. | MMA | BB | 14EG | HEMA | 3G | DMPT |
| L1 | 15 | 69 | 7 | 8 | — | 1 |
| L2 | 44 | 19 | 18 | 18 | — | 1 |
| L3 | 7 | 85 | — | 7 | — | 1 |
| L4 | 50 | 8 | 21 | 20 | — | 1 |
| L5 | 30 | 44 | 12.5 | 12.5 | — | 1 |
| L6 | 30 | 44 | — | — | 25 | 1 |

TABLE 5

| | Element concentration (ppm) | | | | | |
|---|---|---|---|---|---|---|
| | F | B | Al | Si | Sr | Na |
| Example 1 | 0.7 | 2 | 0.8 | 1 | 2.8 | 0.6 |
| Example 2 | 0.7 | 2.1 | 0.9 | 1.3 | 2.6 | 0.8 |
| Example 3 | 3.6 | 6.2 | 2.8 | 3 | 7.8 | 1.9 |
| Example 4 | 3.8 | 6.5 | 3 | 2.8 | 7.9 | 2.1 |
| Example 5 | 2 | 3.9 | 2.5 | 2.3 | 4.4 | 1 |
| Example 6 | 1.7 | 3.6 | 2.2 | 2.1 | 4.8 | 1 |
| Example 7 | 1.8 | 3.8 | 2.3 | 2.3 | 4.6 | 1.1 |
| Example 8 | 2 | 4 | 2.5 | 2.1 | 4.8 | 1 |
| Example 9 | 2.6 | — | — | — | — | 2.1 |
| Example 10 | 4.2 | 4.1 | 2.3 | 2.5 | 4.4 | 3.3 |
| Comparative Example 1 | 0.3 | 0.8 | 0.4 | 0.3 | 0.9 | 0.2 |
| Comparative Example 2 | 0.4 | 0.8 | 0.5 | 0.5 | 1.1 | 0.3 |

TABLE 4

| | Test result | | | | | | | |
|---|---|---|---|---|---|---|---|---|
| | | | | | | Shore D hardness | Acid neutralizing capacity | |
| | Powder | Liquid | Powder-liquid ratio | Removability | Sealability | | After 6 h | After 12 h |
| Example 1 | P1 | L1 | 2/1 | A | B | 38.3 | 4.6 | 5.1 |
| Example 2 | P1 | L2 | 2/1 | B | A | 42.6 | 4.5 | 5.1 |
| Example 3 | P2 | L1 | 2/1 | B | B | 46.1 | 5 | 5.6 |
| Example 4 | P2 | L2 | 2/1 | B | A | 44.8 | 5 | 5.7 |
| Example 5 | P5 | L5 | 2.2/1 | A | A | 45.4 | 4.8 | 5.2 |
| Example 6 | P5 | L5 | 1.8/1 | A | A | 44 | 4.9 | 5.7 |
| Example 7 | P5 | L5 | 2/1 | A | A | 44.5 | 5.1 | 5.8 |
| Example 8 | P6 | L5 | 2/1 | A | A | 44.8 | 4.9 | 5.9 |
| Example 9 | P7 | L5 | 2/1 | A | A | 45.2 | 4.1 | 4.2 |
| Example 10 | P8 | L5 | 2/1 | A | A | 45.5 | 4.7 | 5.1 |
| Comparative Example 1 | P3 | L3 | 2/1 | D | D | 28.3 | 4.2 | 4.5 |
| Comparative Example 2 | P3 | L4 | 2/1 | D | D | 32 | 4.3 | 4.7 |
| Comparative Example 3 | P4 | L3 | 2/1 | D | C | 50.5 | 5.2 | 5.9 |
| Comparative Example 4 | P4 | L4 | 2/1 | D | C | 53.2 | 5.3 | 5.9 |
| Comparative Example 5 | P5 | L6 | 2/1 | C | D | 43.8 | 4.4 | 5.2 |
| Comparative Example 6 | P9 | L5 | 2/1 | D | D | 39 | 5.1 | 5.8 |
| Comparative Example 7 | P10 | L5 | 2/1 | D | D | 45.3 | 4.8 | 5.5 |

TABLE 5-continued

| | Element concentration (ppm) | | | | | |
|---|---|---|---|---|---|---|
| | F | B | Al | Si | Sr | Na |
| Comparative Example 3 | 4.3 | 6.8 | 3.3 | 3.1 | 8.1 | 2 |
| Comparative Example 4 | 4 | 6.8 | 3.5 | 3.3 | 8.2 | 2.3 |
| Comparative Example 5 | 0.3 | 1 | 0.5 | 0.2 | 0.2 | 0.1 |
| Comparative Example 6 | 1.6 | 3.5 | 1.9 | 2.4 | 4.3 | 1.2 |
| Comparative Example 7 | 1.5 | 3.3 | 1.8 | 2.3 | 4.1 | 1.1 |

Examples 1 to 10 are dental resin temporary sealing material compositions each including the constituent features (a) to (f) of the present invention. As shown in Table 4, in the case where the formed cavity was temporarily sealed, pigment invasion was hardly observed, demonstrating excellent sealability. In addition, their proper hardness indicates excellent removability. Examples 5 and 6 respectively have the powder-liquid ratios of 2.2/1 and 1.8/1 assuming clinical fluctuations, but exhibited favorable sealability and removability as temporary sealing materials.

As shown in Table 5, Example 9 released the fluoride ion and the sodium ion, and Examples 1 to 8 and 10 released six types of ions including the fluoride ion. The fluoride ion is expected to strengthen the temporarily sealed cavity wall tooth substance. Moreover, in Examples 1 to 8 and 10, six types of ions were observed from the ion sustained-release glass to exhibit the acid neutralizing capacity. Therefore, not only the tooth substance strengthening effect by the fluoride ion but also the synergic effects with the other ions, such as tooth substance decalcification inhibition, can be expected.

Comparative Examples 1 to 4 exhibited poor removability, sealability, or Shore D hardness because, of the constituent features of the present invention, each component is not in its preferable range. Comparative Example 5 is a system not including a hydrophilic polymerizable monomer, and exhibited poor sealability due to its low wettability with the tooth substance.

Comparative Examples 6 and 7 exhibited poor sealability and removability because, of the constituent features of the present invention, the molecular weight and average particle diameter of PMMA or PEMA as the component (a) are not in their preferable ranges.

The invention claimed is:
1. A dental resin temporary sealing material composition that is polymerizable, the dental resin temporary sealing material composition comprising:
(a) 44% to 64% by weight of a noncrosslinked (meth)acrylate polymer;
(b) 3% to 21% by weight of a filling material;
(c) 4% to 16% by weight of a monofunctional (meth)acrylate polymerizable monomer;
(d) 4% to 13% by weight of a hydrophilic polymerizable monomer;
(e) 0.1% to 5% by weight of a polymerization initiator; and
(f) 5% to 25% by weight of a plasticizer,
wherein the noncrosslinked (meth)acrylate polymer (a) is particulate, has a 50% average particle diameter in a range of 5 μm to 150 μm, and a weight-average molecular weight in a range of 50000 to 1500000, and
the hydrophilic polymerizable monomer (d) has solubility of 5% by weight or more in water at 23° C., and is at least one selected from the group consisting of 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2-hydroxypropyl-1,3-di(meth)acrylate, 3-hydroxypropyl-1,2-di(meth)acrylate, pentaerythritol di(meth)acrylate, 2-trimethylammoniumethyl (meth)acrylchloride, (meth)acrylamide, 2-hydroxyethyl (meth)acrylamide, and polyethylene glycol di(meth)acrylate, wherein a number of oxyethylene groups is greater than or equal to 9.

2. The dental resin temporary sealing material composition according to claim 1,
wherein a part or whole of the filling material (b) is ion sustained-release glass.

3. The dental resin temporary sealing material composition according to claim 2,
wherein the ion sustained-release glass sustained-releases a fluoride ion, and further sustained-releases at least one ion from among bivalent to tetravalent ions.

4. The dental resin temporary sealing material composition according to claim 2,
wherein the ion sustained-release glass sustained-releases a fluoride ion, and further sustained-releases at least one ion from among a strontium ion, an aluminum ion, and a borate ion.

* * * * *